United States Patent [19]

Sano et al.

[11] Patent Number: 5,011,980

[45] Date of Patent: Apr. 30, 1991

[54] PROCESS FOR PREPARATION OF ALLYL ACETATE

[75] Inventors: Kenichi Sano; Kenichiro Maki; Hideyuki Kamei, all of Oita, Japan

[73] Assignee: Showa Denko K.K., Tokyo, Japan

[21] Appl. No.: 413,498

[22] Filed: Sep. 27, 1989

[30] Foreign Application Priority Data

Sep. 29, 1988 [JP] Japan .................... 63-242471

[51] Int. Cl.$^5$ .............................. C07C 67/05
[52] U.S. Cl. ...................... 560/245; 502/151; 502/170
[58] Field of Search .......................... 560/245

[56] References Cited

U.S. PATENT DOCUMENTS

| | | | |
|---|---|---|---|
| 3,300,528 | 1/1967 | Wakasa | 560/245 |
| 3,917,676 | 11/1975 | Kisaki | 560/245 |
| 3,970,713 | 7/1976 | Scharfe | 560/245 |
| 4,634,794 | 1/1987 | Drake | 560/245 |
| 4,647,690 | 3/1987 | Drake | 560/245 |

Primary Examiner—Michael L. Shippen

Attorney, Agent, or Firm—Sughrue, Mion, Zinn, Macpeak & Seas

[57] ABSTRACT

A catalyst prepared by (a) impregnating a catalyst carrier with an aqueous solution of a palladium salt and a salt of at least one metal selected from the group consisting of copper, lead, ruthenium and rhenium in an amount corresponding to 90 to 95% of the water absorption of the carrier, (b) treating the impregnated carrier with an aqueous solution of an alkali metal salt in an amount corresponding to 120 to 500% of the water absorption of the carrier to precipitate water-insoluble compounds of palladium and at least one metal selected from the group consisting of copper, lead, ruthenium and rhenium on the carrier, (c) treating the metal compounds-deposited carrier with a reducing agent to convert the compounds to the corresponding metals, and (d) further supporting an alkali metal acetate on the carrier, had a high catalytic activity for the reaction of forming allyl acetate by reacting propylene, acetic acid and oxygen in the gas phase, and the selectivity to allyl acetate is very high and the life of this catalyst is long.

9 Claims, No Drawings

PROCESS FOR PREPARATION OF ALLYL ACETATE

BACKGROUND OF THE INVENTION

1. Field of the Invention

The present invention relates to a process for preparing allyl acetate from propylene, acetic acid and oxygen in the gas phase.

2. Description of the Related Art

Many reports have been published on catalysts to be used for preparing allyl acetate from propylene, acetic acid and oxygen in the gas phase. Most of these catalysts comprise palladium as the main catalyst and at least one metal selected from the group consisting of alkali metals, alkaline earth metals, gold, copper, molybdenum, cadmium, lead, vanadium, bismuth, chromium, tungsten, manganese and iron as the promoter, and these catalyst components are usually supported on alumina, silica, active carbon, pumice, titanium oxide or the like.

When carrying out a reaction by using these catalysts, it is industrially important that the activity of the catalyst is high, the change of the activity over a long period is small, and the selectivity to allyl acetate is high.

Studies of the promoter and carrier are important for obtaining a catalyst having a high activity, a long life, and a high selectivity, but studies on the catalyst-preparing process are as important as the above-mentioned studies. It is broadly and empirically recognized that, even if the catalyst components and carrier are the same, often the reaction results differ greatly due to differences in the catalyst-preparing process.

Accordingly, various proposals have been made with regard to the promoter component, the carrier and the catalyst-preparing process, for improving the catalyst performances such as the activity, and a uniform support of palladium on the carrier is recommended (see, for example, Japanese Examined Patent Publication No. 44-29046, No. 46-23364, No. 50-5685, No. 52-29294 and No. 55-27046, and Japanese Unexamined Patent Publication No. 48-64014, No. 60-32747 and No. 61-238759).

In each of these conventional catalysts, however, the amount of allyl acetate formed in 1 hour per gram of metallic palladium (hereinafter referred to as "relative activity") does not exceed 70 g, and since palladium metal is very expensive, it is considered that the contact efficiency per unit weight of metallic palladium is too low for conducting the preparation of allyl acetate on an industrial scale.

SUMMARY OF THE INVENTION

Therefore, a primary object of the present invention is to provide a process in which allyl acetate is industrially advantageously prepared by reacting propylene, acetic acid and oxygen in the gas phase.

The present inventors carried out into ways of enhancing the activity (especially the relative activity) of the catalyst to be used when preparing allyl acetate from propylene, acetic acid and oxygen by a gas-phase reaction, to realize the above object, and as a result, found that a catalyst prepared by (a) impregnating a catalyst carrier with an aqueous solution of a palladium salt and a salt of at least one metal selected from the group consisting of copper, lead, ruthenium and rhenium in an amount corresponding to 90 to 95% of the water absorption of the carrier, (b) treating the impregnated carrier with an aqueous solution of an alkali metal salt in an amount corresponding to 120 to 500% of the water absorption of the carrier to precipitate water-insoluble compounds of palladium and at least one metal selected from the group consisting of copper, lead, ruthenium and rhenium on the carrier, (c) treating the metal compounds-deposited carrier with a reducing agent to convert the compounds to the corresponding metals, and (d) further supporting an alkali metal acetate on the carrier, has a very high activity (especially, a high relative activity). The present invention was completed based on this finding.

More specifically, in accordance with the present invention, there is provided a process for the gas phase synthesis of allyl acetate, which comprises reacting propylene, acetic acid and oxygen in the gas phase in the presence of a catalyst prepared by impregnating a catalyst carrier with an aqueous solution of a palladium salt and a salt of at least one metal selected from the group consisting of copper, lead, ruthenium and rhenium in an amount corresponding to 90 to 95% of the water absorption of the carrier, treating the impregnated carrier with an aqueous solution of an alkali metal salt in an amount corresponding to 120 to 500% of the water absorption of the carrier to precipitate water-insoluble compounds of palladium and at least one metal selected from the group consisting of copper, lead, ruthenium and rhenium on the catalyst carrier, treating the metal compounds-deposited carrier with a reducing agent to convert the compounds to the corresponding metals, and further, supporting an alkali metal acetate on the carrier.

Note, Japanese Examined Patent Publication No. 59-46668 discloses a process for preparing a catalyst for the gas phase synthesis of allyl acetate from propylene, in which the step of impregnating a carrier with catalyst components is carried out by using an aqueous solution of palladium and a gold compound in an amount corresponding to about 95 to about 100% of the absorption capacity (that is, the water absorption) of the carrier and the subsequent precipitation step is carried out by immersing the wet impregnated catalyst in a solution of an alkali metal silicate. As a result of tracing experiments by the present inventors, it was found that palladium is thinly distributed in the surface layer of the carrier in the obtained catalyst, the activity of forming allyl acetate is not high enough, the selectivity is extremely low, and only unsatisfactory results are obtained.

DESCRIPTION OF THE PREFERRED EMBODIMENTS

The most characteristic feature of the catalyst used in the present invention resides in that, even though palladium is supported in the surface layer of the carrier, the selectivity to allyl acetate is high and the activity of forming allyl acetate is much higher than those of the conventional catalysts. Namely, in the case of the catalyst used in the present invention, even if the content of metallic palladium is as low as 3.3 g per liter of the catalyst, the space time yield of allyl acetate is at least 600 g/liter of the catalyst per hour and the amount of allyl acetate formed for 1 hour per gram of metallic palladium (relative activity) is as large as 180 g or more. Furthermore, since the catalyst activity is high, a sufficient yield is obtained even at a reaction temperature of 140° to 160° C. Accordingly, the reaction can be carried out at a temperature lower than the optimum reaction temperature of 170° to 200° C. for the conventional catalysts. This means that the selectivity is increased if the comparison is based on the same relative activity, and the risk of corrosion of a reaction apparatus caused by using acetic acid having a high corrosive action as the reactant can be reduced.

Moreover, the catalyst used in the process of the present invention has a very high selectivity to allyl acetate, and the main by-product formed at the reaction is a small amount of carbon dioxide, and the catalyst is advantageous in that a compound which cannot be easily separated is not formed as a by-product. Furthermore, the catalyst used in the present invention has an excellent catalyst life, which is an important factor for industrial catalysts.

The process for the preparation of the catalyst will now be described in detail.

In the present invention, first an appropriate catalyst carrier is impregnated with an aqueous solution of a palladium salt and a salt of at least one metal selected from the group consisting of copper, lead, ruthenium and rhenium. As the catalyst carrier, there can be mentioned alumina, silica, active carbon, silica-alumina, pumice and titanium oxide. In view of the stability against acetic acid, silica and titanium oxide are especially preferred. As the palladium salt, there can be used soluble salts such as palladium chloride, palladium sodium chloride, palladium nitrate, palladium sulfate and palladium acetate. Palladium sodium chloride has an especially excellent water solubility. As the salts of copper, lead, ruthenium and rhenium, there can be used soluble salts such as nitrates, carbonates, sulfates, organic acid salts and halides. In general, chlorides are preferable because they are easily available and have an excellent water solubility.

Preferably, the amount supported of palladium and the amount supported of copper, lead, ruthenium or rhenium as the promoter based on the weight of the carrier, is 0.1 to 5.0% by weight, especially 0.3 to 1.0% by weight, and 0.01 to 5.0% by weight, especially 0.02 to 1.0% by weight, respectively. Also, preferably the ratio of the promoter element (copper, lead, ruthenium or rhenium) to palladium in the catalyst is such that the amount of the promoter element is 0.05 to 10 gram-atoms, especially 0.1 to 5 gram-atoms, per gram-atom of palladium. The amount of the aqueous solution used for impregnating the carrier with the palladium salt and the salt of at least one metal selected from the group consisting of copper, lead, ruthenium and rhenium is advantageously 90 to 95% of the water absorption of the carrier. If the amount of the aqueous solution is too large or too small, the catalyst components such as palladium are not uniformly supported on the carrier and the catalyst performances are adversely influenced.

Then, the carrier impregnated with the catalyst solution is treated with an aqueous solution of an alkali metal salt. Preferably, the carrier impregnated with the catalyst solution is alkali-treated without drying. The reason for this has not been elucidated, but it is assumed that, if this drying is carried out, the reaction between the catalyst component and the alkali is adversely influenced by the drying and palladium is not supported in a highly dispersed state in the surface layer of the carrier.

As the alkali metal salt, water-soluble salts such as hydroxides, silicates, carbonates and bicarbonates can be used, but in general, the use of alkali metal hydroxides and alkali metal silicates, which are easily available and have a high purity, is preferred.

Preferably, the amount of the alkali metal salt contained in the aqueous solution of the alkali metal salt is 1 to 10 times, especially 1 to 3 times, the stoichiometric amount necessary for a formation of water-insoluble compounds by the reaction with the compounds of the catalyst components contained in the carrier impregnated with the solution of the catalyst components. If the amount of the alkali metal salt is too small and below this range, the reaction between the catalyst component and the alkali is incomplete and the subsequent reduction reaction is adversely influenced. Furthermore, if the amount of the alkali metal is too large and exceeds the above-mentioned range, the reaction between the catalyst component and the alkali is abrupt. In each case, palladium is not supported in a highly dispersed state in the surface layer of the carrier.

Preferably, the amount of the aqueous solution of the alkali metal salt is 120 to 500%, especially 150 to 250%, of the water absorption of the carrier. It has been found that the amount of the aqueous solution of the alkali metal salt is very important for the preparation of the catalyst. More specifically, only when the amount of the aqueous solution of the alkali metal salt is within the above-mentioned range, is the palladium supported in a highly dispersed state in the surface layer of the catalyst. If the amount of the aqueous solution of the alkali metal salt is below the above-mentioned range, palladium is not allowed to move to the surface layer of the carrier but is supported in the interior of the carrier, and if the amount of the aqueous solution of the alkali metal salt exceeds the above-mentioned range, a cohesion of palladium occurs and the palladium is not supported in a highly dispersed state. To increase the activity (especially the relative activity) of the catalyst, preferably the palladium is supported in a highly dispersed state in the surface layer of the carrier, and accordingly, the adjustment of the amount of the aqueous solution of the alkali metal salt is very important.

The time of the treatment with the aqueous solution of the alkali metal salt is that necessary for completely converting the salts of the catalyst components contained in the carrier impregnated with the catalyst solution to water-insoluble compounds. A treatment time of 20 hours is generally sufficient.

Then, the compounds of the metals of the catalyst components, deposited in the surface layer of the catalyst carrier, are treated with a reducing agent. The reduction treatment is generally carried out in the liquid phase by an addition of a reducing agent such as hydrazine or formalin. Then the treated carrier is washed with water until the chlorine ion is not detected, the carrier is dried, an alkali metal acetate is supported on the carrier, and the carrier is dried again.

The catalyst prepared according to the above-mentioned procedures is characterized in that, even though palladium is distributed in the surface layer of the catalyst carrier, the activity of forming allyl acetate is very high and the selectivity to allyl acetate can be maintained at a level higher than 92%.

When carrying out the process of the present invention, the use of propylene having a high purity as the starting propylene is advantageous, but an incorporation of a small amount of a lower saturated hydrocarbon such as methane, ethane or propane is permissible.

Even if small amounts of impurities such as acetaldehyde and water are included in the starting acetic acid, no problem arises when carrying out the process of the present invention. Concentrated acetic acid, for example, glacial acetic acid, is preferably used. Oxygen can be supplied in the state diluted with an inert gas such as nitrogen or carbon dioxide gas, for example, in the form of air. Where the reaction gas is circulated, the use of oxygen having a high concentration, especially a concentration higher than 99%, is recommended.

In the process of the present invention, the gases supplied to the reaction system are substantially propylene, acetic acid, oxygen, and a diluent gas. These gases are supplied to the reaction system so that the amounts of propylene, acetic acid and oxygen are 5 to 50% by volume, preferably 10 to 40% by volume, 5 to 20% by volume, preferably 6 to 10% by volume, and 3 to 15% by volume, preferably 5 to 10% by volume, respectively, based on the total amount of the gases.

During the reaction, sometimes the alkali metal acetate supported on the catalyst carrier is dissociated little by little and flows out of the reaction system. Accordingly, to maintain the amount of the alkali metal acetate supported in the catalyst within the desired range, there can be adopted, for example, a method in which the alkali metal acetate in the form of an aqueous solution or a solution in acetic acid is added to the supply gas during the reaction.

When preparing allyl acetate by reacting propylene, acetic acid and oxygen according to the process of the present invention, the reaction temperature is 100° to 200° C., but a reaction temperature of 140° to 170° C. is practically advantageous. In view of the reaction equipment, a reaction pressure of from the atmospheric pressure to 30 atmospheres is practically advantageous, and a reaction pressure of 2 to 10 atmospheres is especially preferred.

A fixed bed reaction method, a fluidized bed reaction method and the like can be adopted as the reaction method, but the adoption of a fixed bed comprising the above-mentioned catalyst packed in a reaction tube having a corrosion resistance is practically advantageous.

The present invention will now be described in detail with reference to the following examples, that by no means limit the scope of the invention.

EXAMPLE 1

To 36 ml (corresponding to 90% of the water absorption of the carrier) of an aqueous solution containing 0.912 g of sodium tetrachloropalladate ($Na_2PdCl_4$) and 0.104 g of copper chloride ($CuCl_2$) was added 100 ml of a silica carrier having a particle size of 5 mm, and the carrier was completely impregnated with the aqueous solution. Then the impregnated carrier was added to 80 ml (corresponding to 200% of the water absorption of the carrier) of an aqueous solution containing 0.591 g of sodium hydroxide and the alkali treatment was carried out at room temperature for 20 hours, hydrazine hydrate was added, and the reducing treatment was carried out. After the reducing treatment, the catalyst was washed with water until the chlorine ion was not detected, and then the catalyst was dried at 110° C. for 4 hours. The catalyst was then thrown into 36 ml of an aqueous solution containing 3 g of potassium acetate (KOAc) and all of the aqueous solution was absorbed in the catalyst, and the catalyst was dried again at 110° C. for 20 hours.

By examination using an X-ray microanalyzer and a microscope, it was confirmed that, in the obtained catalyst, palladium was supported in the surface layer of the carrier. A stainless steel reaction tube having an inner diameter of 21.4 mm was packed with 20 ml of the catalyst, and a gas mixture comprising 30% of propylene, 7.0% of acetic acid, 7.0% of oxygen, 14.0% of water, and 42.0% of nitrogen was supplied at a speed of 42 Nl/hr. The reaction was carried out under the conditions of a reaction temperature of 165° C. and a pressure of 5 atmospheres (gauge pressure). The results are shown in Table 1.

COMPARATIVE EXAMPLE 1

A catalyst was prepared in the same manner as described in Example 1 except that 0.319 g of chloroauric acid ($HAuCl_4 \cdot 4H_2O$) was used instead of copper chloride according to the teaching of Japanese Examined Patent Publication No. 59-46668. Using the obtained catalyst, the reaction of the synthesis of allyl acetate was carried out under the same conditions as described in Example 1. The results are shown in Table 1.

COMPARATIVE EXAMPLE 2

A catalyst was prepared in the same manner as described in Example 1 except that the amount used of the aqueous solution containing sodium hydroxide was changed to 40 ml (corresponding to the water absorption of the carrier) from 80 ml and the treated carrier was then dried. Using the obtained catalyst, the reaction was carried out under the same conditions as described in Example 1. The results are shown in Table 1.

COMPARATIVE EXAMPLE 3

The carrier was impregnated with the palladium salt and copper salt in the same manner as described in Example 1, and the impregnated carrier was dried at 110° C. for 4 hours. The dried carrier was thrown into an aqueous solution containing sodium hydroxide and hydrazine hydrate, and the reduction treatment was carried out. Other conditions for the preparation of the catalyst were the same as described in Example 1. In the obtained catalyst, palladium was uniformly supported on the carrier. Using the obtained catalyst, the reaction was carried out under the same conditions as described in Example 1. The results are shown in Table 1.

COMPARATIVE EXAMPLE 4

A catalyst was prepared in the same manner as described in Example 1 except that potassium acetate was not supported. Using the obtained catalyst, the reaction was carried out under the same conditions as described in Example 1. The results are shown in Table 1.

COMPARATIVE EXAMPLE 5

A catalyst was prepared in the same manner as described in Example 1 except that copper chloride was not supported. Using the obtained catalyst, the reaction was carried out under the same conditions as described in Example 1. The results are shown in Table 1.

EXAMPLE 2

A catalyst was prepared in the same manner as described in Example 1 except that 2.1 g of sodium metasilicate was used instead of sodium hydroxide. Using the obtained catalyst, the reaction was carried out under the same conditions as described in Example 1. The results are shown in Table 1.

EXAMPLE 3

A catalyst was prepared in the same manner as described in Example 2 except that 6 g of potassium acetate was used. Using the obtained catalyst, the reaction was carried out under the same conditions as described in Example 1. The results are shown in Table 1.

EXAMPLE 4

Pelletized titania having a diameter of 3 mm and a length of 3 to 5 mm, which had been heat-treated at 800° C., was used instead of the silica carrier used in Example 1. More specifically, 100 ml of this titania carrier was added to 32 ml (corresponding to 91% of the water absorption of the carrier) of an aqueous solution containing 0.912 g of sodium tetrachloropalladate and 0.104 g of copper chloride and the carrier was completely impregnated with the aqueous solution. Then the impregnated carrier was added to 70 ml (corresponding to 200% of the carrier) of an aqueous solution containing 0.591 g of sodium hydroxide, and the alkali treatment was carried out at room temperature for 20 hours, and reduction with hydrazine, water washing and drying were carried out in the same manner as described in Example 1. Then the treated carrier was thrown into 32 ml of an aqueous solution containing 3 g of potassium acetate and all of the aqueous solution was absorbed in the carrier, and the carrier was dried at 110° C. for 20 hours. Using the obtained catalyst, the reaction was carried out under the same conditions as described in Example 1. The results are shown in Table 1.

EXAMPLE 5

A catalyst was prepared in the same manner as described in Example 1 except that 0.215 g of lead chloride ($PbCl_2$) was used instead of copper chloride. Using the obtained catalyst, the reaction was carried out under the same conditions as described in Example 1. The results are shown in Table 1.

EXAMPLE 6

A catalyst was prepared in the same manner as described in Example 5 except that 2.1 g of sodium metasilicate was used instead of sodium hydroxide. Using the obtained catalyst, the reaction was carried out under the same conditions as described in Example 1. The results are shown in Table 1.

EXAMPLE 7

A catalyst was prepared in the same manner as described in Example 1 except that 0.258 g of ruthenium chloride ($RuCl_4 \cdot 5H_2O$) was used instead of copper chloride. Using the obtained catalyst, the reaction was carried out under the same conditions as described in Example 1. The results are shown in Table 1.

EXAMPLE 8

A catalyst was prepared in the same manner as described in Example 2 except that 0.226 g of rhenium chloride ($ReCl_3$) was used instead of copper chloride. Using the obtained catalyst, the reaction was carried out under the same conditions as described in Example 1. The results are shown in Table 1.

EXAMPLE 9

A catalyst was prepared in the same manner as described in Example 2 except that 0.072 g of copper chloride and 6 g of potassium acetate were used. A stainless steel reaction tube having an inner diameter of 25 mm was packed with 50 ml of the obtained catalyst, and a gas mixture comprising 30% of propylene, 9.8% of acetic acid, 7.0% of oxygen, 14.0% of water and 39.2% of nitrogen was supplied at a speed of 315 Nl/hr. The reaction was carried out under a reaction pressure of 5 atmospheres (gauge pressure) in the state where the highest temperature in the catalyst layer was 160° C. When 150 hours had passed from the point of the start of the reaction, the allyl acetate-forming speed (STY) was 610 g/l hr, the relative activity was 185 (allyl acetate/g of Pd per hour), and the selectivity to allyl acetate was 96.9%. The reaction was further conducted, and even after 1500 hours, the allyl acetate-forming speed and selectivity were not changed.

TABLE 1

| | STY (g/l · hr) of Allyl Acetate | Relative Activity (g/g − Pd · hr) | Selectivity (%) to Allyl Acetate | Remarks |
| --- | --- | --- | --- | --- |
| Example 1 | 507 | 154 | 94.4 | |
| Comparative Example 1 | 273 | 83 | 87.5 | Au was used as promoter |
| Comparative Example 2 | 290 | 88 | 94.0 | Aqueous alkali solution was used in amount corresponding to water absorption of carrier |
| Comparative Example 3 | 141 | 43 | 95.5 | Intermediate drying was carried out, and alkali treatment and reducing treatment were simultaneously carried out |
| Comparative Example 4 | 105 | 32 | 78.0 | Alkali metal acetate was not added |
| Comparative Example 5 | 285 | 86 | 87.0 | promoter was not added |
| Example 2 | 403 | 122 | 94.8 | |
| Example 3 | 484 | 147 | 94.0 | |
| Example 4 | 431 | 131 | 93.5 | |
| Example 5 | 462 | 140 | 94.7 | |
| Example 6 | 385 | 117 | 95.1 | |
| Example 7 | 419 | 127 | 91.7 | |
| Example 8 | 375 | 114 | 94.2 | |

We claim:

1. A process for the gas phase synthesis of allyl acetate, which comprises reacting propylene, acetic acid and oxygen in the gas phase in the presence of a catalyst prepared by impregnating a catalyst carrier with an aqueous solution of a palladium salt and a salt of at least one metal selected from the group consisting of copper, lead, ruthenium and rhenium in an amount corresponding to 90 to 95% of the water absorption of the carrier, treating the impregnated carrier with an aqueous solution of an alkali metal salt in an amount corresponding to 120 to 500% of the water absorption of the carrier to precipitate water-insoluble compounds of palladium and at least one metal selected from the group consisting of copper, lead, ruthenium and rhenium on the catalyst carrier, treating the metal compounds-deposited carrier with a reducing agent to convert the compounds to the corresponding metals, and further supporting an alkali metal acetate on the carrier.

2. A process for the gas phase synthesis of allyl acetate according to claim 1, wherein the catalyst carrier is selected from the group consisting of alumina, silica, active carbon, silica-alumina, pumice and titanium oxide.

3. A process for the gas phase synthesis of allyl acetate according to claim 1, wherein the palladium salt is selected from the group consisting of palladium chloride, palladium sodium chloride, palladium nitrate, palladium sulfate and palladium acetate.

4. A process for the gas phase synthesis of allyl acetate according to claim 1, wherein the salts of copper, lead, ruthenium and rhenium are selected from their nitrates, carbonates, sulfates, organic acid salts and halides.

5. A process for the gas phase synthesis of allyl acetate according to claim 1, wherein, based on the weight of the carrier, the amount of palladium supported is 0.1–5.0% by weight and the amount of copper, lead, ruthenium or rhenium supported is 0.01–5.0% by weight.

6. A process for the gas phase synthesis of allyl acetate according to claim 1, wherein the ratio of copper, lead ruthenium or rhenium to palladium in the catalyst is 0.05–10 gram-atoms per gram-atom of palladium.

7. A process for the gas phase synthesis of allyl acetate according to claim 1, wherein the catalyst carrier impregnated with the aqueous solution of the metal salts is treated with an aqueous solution of an alkali metal salt without drying.

8. A process for the gas phase synthesis of allyl acetate according to claim 1, wherein the alkali metal salt is selected from the group consisting of alkali metal hydroxides, silicates, carbonates and bicarbonates.

9. A process for the gas phase synthesis of allyl acetate according to claim 1, wherein the amount of the alkali metal salt contained in the aqueous alkali metal salt solution is 1 to 10 times the stoicheometric amount necessary for formation of the water insoluble compounds.

* * * * *